US009504784B2

(12) United States Patent
Ozturk (10) Patent No.: US 9,504,784 B2
(45) Date of Patent: Nov. 29, 2016

(54) PERISTALTIC PUMP WITH MULTIPLE INDEPENDENT CHANNELS

(75) Inventor: Gunay Ozturk, Coupeville, WA (US)

(73) Assignee: Cole-Parmer Instrument Company LLC, Barrington, IL (US)

( * ) Notice: Subject to any disclaimer, the term of this patent is extended or adjusted under 35 U.S.C. 154(b) by 1102 days.

(21) Appl. No.: 13/200,029

(22) Filed: Sep. 15, 2011

(65) Prior Publication Data

US 2013/0072871 A1    Mar. 21, 2013

(51) Int. Cl.
*A61M 1/00*      (2006.01)
*F04B 43/12*     (2006.01)
*A61M 5/142*     (2006.01)

(52) U.S. Cl.
CPC ..... *A61M 5/14232* (2013.01); *A61M 5/14228* (2013.01); *F04B 43/1253* (2013.01); *F04B 43/1261* (2013.01); *F04B 43/1292* (2013.01)

(58) Field of Classification Search
CPC .................... A61M 5/14228; A61M 5/14232; F04B 43/1292; F04B 43/1261; F04B 43/1253
USPC ............................. 604/123, 4.01; 417/477.2
See application file for complete search history.

(56) References Cited

U.S. PATENT DOCUMENTS

| | | | | |
|---|---|---|---|---|
| 4,004,035 A | * | 1/1977 | Hirzel et al. .................. | 426/275 |
| 4,189,067 A | * | 2/1980 | Nottke et al. .................. | 222/57 |
| 5,098,261 A | * | 3/1992 | Bertoncini ..................... | 417/475 |
| 5,318,413 A | * | 6/1994 | Bertoncini ..................... | 417/475 |
| 6,695,803 B1 | * | 2/2004 | Robinson ................ | A61M 1/02 210/252 |
| 7,214,038 B2 | * | 5/2007 | Saxer et al. ................ | 417/477.2 |
| 8,246,321 B2 | * | 8/2012 | Miyazaki et al. ............ | 417/316 |
| 2003/0224105 A1 | * | 12/2003 | Chondroudis et al. ....... | 427/240 |
| 2007/0217932 A1 | | 9/2007 | Voyeux et al. | |
| 2009/0035165 A1 | * | 2/2009 | Chang ........................ | 417/477.2 |
| 2009/0208350 A1 | * | 8/2009 | Miyazaki et al. ............ | 417/316 |
| 2011/0004143 A1 | | 1/2011 | Beiriger et al. | |

FOREIGN PATENT DOCUMENTS

| | | | | |
|---|---|---|---|---|
| JP | 2002-527212 | | 8/2002 | |
| JP | 2006-242116 | | 9/2006 | |
| JP | 2006242116 A | * | 9/2006 | ................ F04C 5/00 |
| JP | 2008-503688 | | 2/2008 | |
| WO | 00/23140 | | 4/2000 | |

OTHER PUBLICATIONS

International Search Report and Writen Opinion of the International Searching Authority, International Patent Application PCT/US2012/055475, Mar. 15, 2013.

* cited by examiner

*Primary Examiner* — Laura Bouchelle
*Assistant Examiner* — Anh Bui
(74) *Attorney, Agent, or Firm* — Vinson & Elkins LLP (57) ABSTRACT

A multi-channel peristaltic pump in which each channel can be operated independently of the others. A peristaltic pump includes a plurality of motors, each of which drives a rotor shaft which is independently rotatable around an axis and which rotates a roller head having a plurality of rollers. The rotor shafts are disposed in a concentric manner. The peristaltic pump further can include a control system allowing an operator to selectively determine the speed and direction of rotation of each of the roller heads of the pump.

25 Claims, 6 Drawing Sheets

PERISTALTIC PUMP WITH MULTIPLE INDEPENDENT CHANNELS

CROSS-REFERENCE TO RELATED APPLICATION

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

FIELD OF THE INVENTION

The present invention relates to pumps, such as those for analytical instruments, and more particularly to peristaltic pumps and methods of using the same, including in connection with analytical instruments and systems, and further including multi-channel peristaltic pumps.

BACKGROUND OF THE INVENTION

Peristaltic pumps have been used in the past to provide a positive displacement of fluids to achieve pumping of the fluids. In conventional peristaltic pumps, a fluid within a flexible tube fitted within a casing is typically used. In such pumps, one or more rollers or shoes are rotated within the casing and compress the tube; as the roller or shoe compresses the tube in one location, the compression forces the movement of the fluid within the tube. Once the roller passes the location, the absence of fluid within the tube in that location induces the flow of fluid to that location in the tube. In conventional applications, the fluid to be pumped with a peristaltic pump is often sterile or of such a nature that it is desirable to avoid having the fluid contact any of the pump. Peristaltic pumps are useful for a wide variety of applications, including dialysis machines, metering pumps, dosing pumps, heart bypass pump machines, drug dispensing systems, infusion pumps, aquariums, analytical instruments, food and pharmaceutical manufacturing operations, and so forth.

In some applications, it is desirable to have a peristaltic pump which has multiple heads, each having multiple rollers. In such pumps, it is therefore possible to simultaneously pump fluids located within multiple tubes. Such peristaltic pumps are sometimes said to have multiple channels. In addition, cartridges have been used in some conventional peristaltic pumps to make it easier to connect and disconnect tubing from the pump. For example, U.S. Pat. No. 7,214,038, issued on May 8, 2007, to Saxer et al., which is hereby incorporated by reference herein, discloses a removable cartridge which can be connected or disconnected from a peristaltic pump by a user with relative ease. Such a peristaltic pump and cartridges for same are commercially available from Ismatec, S.A., of Glattbrugg, Switzerland. In such conventional peristaltic pumps, it is conventional to have a single rotor which drives a shaft having one or more heads, with each head having a plurality of rollers. However, such multiple heads cannot be rotated independently of one another, such as a different speeds or the like.

Attempts to provide individual control over the pumping action in multiple channel peristaltic pumps have been made in the past. For example, in U.S. Pat. No. 5,098,261, issued on Mar. 24, 1992, to Bertoncini, which is hereby incorporated by reference herein, a peristaltic pump is disclosed that includes elastic tubes that are stretched to varying degrees and, as a result of the Poisson effect from such stretching, reduces the flow path cross-section area in the tubes to varying degrees, in an attempt to allow variable flow speeds in the tubing located in different channels in the pump.

Still another approach to provide independent control of the channels in a multiple channel peristaltic pump is provided in U.S. published patent application No. 2009/0035165, published Feb. 9, 2009, and listing Chang as an inventor, which is hereby incorporated by reference herein. In Chang, one or more roller segments are selectively locked or decoupled from a drive shaft and can be operated with a desired speed and direction. The pump shown in Chang includes two motors: one for selecting the channel or channels to be driven by a lead screw and the second for rotating the roller heads.

Yet another example of a multi-channel peristaltic pump is described in U.S. published patent application No. 2001/0004143, which was published on Jan. 6, 2011, and names Beiriger et al as inventors, and which is incorporated by reference herein. In Beiriger et al., a multi-channel peristaltic pump is described with individually controlled rollers, which are free to rotate on a single shaft, and each of which is coupled to a worm gear. This approach describes control of the individual channels through the use of independent motors. However, this approach requires a fairly large device in order to accommodate the motors required and the gear mechanisms to translate the motor's rotation to the rollers. In this approach, the rollers need to be spaced further apart than may be desired.

Another example of a multi-channel peristaltic pump used in a blood processing system is described in U.S. Pat. No. 6,695,803, issued on Feb. 24, 2004 to Robinson et al., which is incorporated by reference herein. In Robinson et al., a blood processing system including a peristaltic pump is described with three rollers which are coupled to three different motors and which share a single support shaft which is also used to rotate one of the rollers, with the two other rollers having hollow shafts through which the support shaft extends, with each of these two rollers able to rotate independently of the roller attached to the support shaft.

However, none of the conventional pumps provide as much flexibility and ease of operation as may be desirable, such as by providing a multi-channel peristaltic pump such that an operator can selectively control the speed and direction of fluid flow in each of the channels independent of the other channels. Moreover, none of the conventional pumps provide such flexibility and do so with a compact size.

SUMMARY OF THE INVENTION

In one embodiment, a multi-channel peristaltic pump is provided which comprises a plurality of channels, with each channel having a roller head with a plurality of rollers, and with each of the heads operable to rotate independently of one another, including at different speeds and in different directions, thus allowing the operator to independently control the speed, amount and direction of fluid flow independently in each of the channels in the multi-channel pump. The pump includes a plurality of concentric, nested drive shafts, with each of the drive shafts adapted to drive a corresponding roller head. Each of the drive shafts can be coupled to a motor, such as by a pulley or timing belt, with the motor being independently actuated and controlled by a user. A control system with a processor and memory and user input can be used to easily allow the operator to selectively operate the roller heads independently of one another. In another embodiment, a method is provided for controlling the speed and direction of the rollers on a plurality of roller heads in a multi-channel peristaltic pump, including the steps of selecting the speed, direction, or other parameters for the operation of the roller heads.

It is an object to provide a multi-channel peristaltic pump in which the user can independently control the operation of each channel, and to do so without requiring a larger amount of space for multiple motors for the channels.

It is yet another object to provide a multi-channel peristaltic pump in which the rollers of the heads are located sufficiently close so that removable cartridges can be used in connection with some or all of said heads.

It is yet another object to minimize the space required for a multi-channel peristaltic pump with a plurality of independently operable channels, and further, to do so in a manner that nonetheless presents a greater surface area of the rollers of one or more channels for pumping action.

These and other advantages will be apparent from the following detailed description and drawings of the illustrative embodiments of the present invention provided.

DETAILED DESCRIPTION

Figure 1:
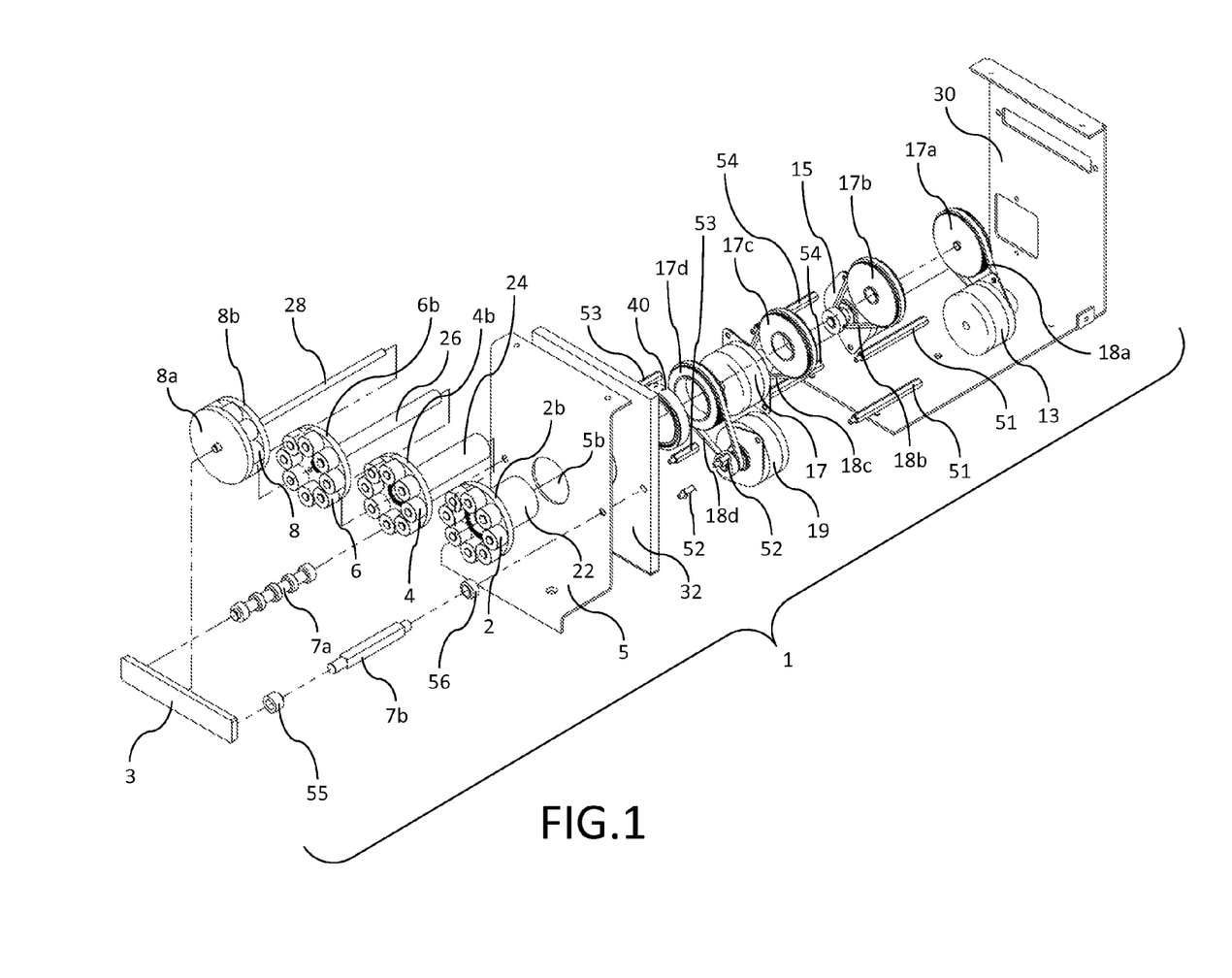
FIG. 1 provides an exploded isometric view of one embodiment of a multi-channel peristaltic pump.

In FIG. 1, a multi-channel peristaltic pump 1 is shown. In FIG. 1, the pump 1 includes a housing, which has a face 5. The pump 1 also has four roller heads 2, 4, 6, and 8, which are shown extending from face 5. In addition, the pump 1 includes supports 7a and 7b which are located on opposite sides of the roller heads 2, 4, 6, and 8. In addition, a support 3 is provided to which supports 7a and 7b are connected. As will be discussed in more detail below, each of roller heads 2, 4, 6, and 8 is rotatable around an axis.

Figure 2:
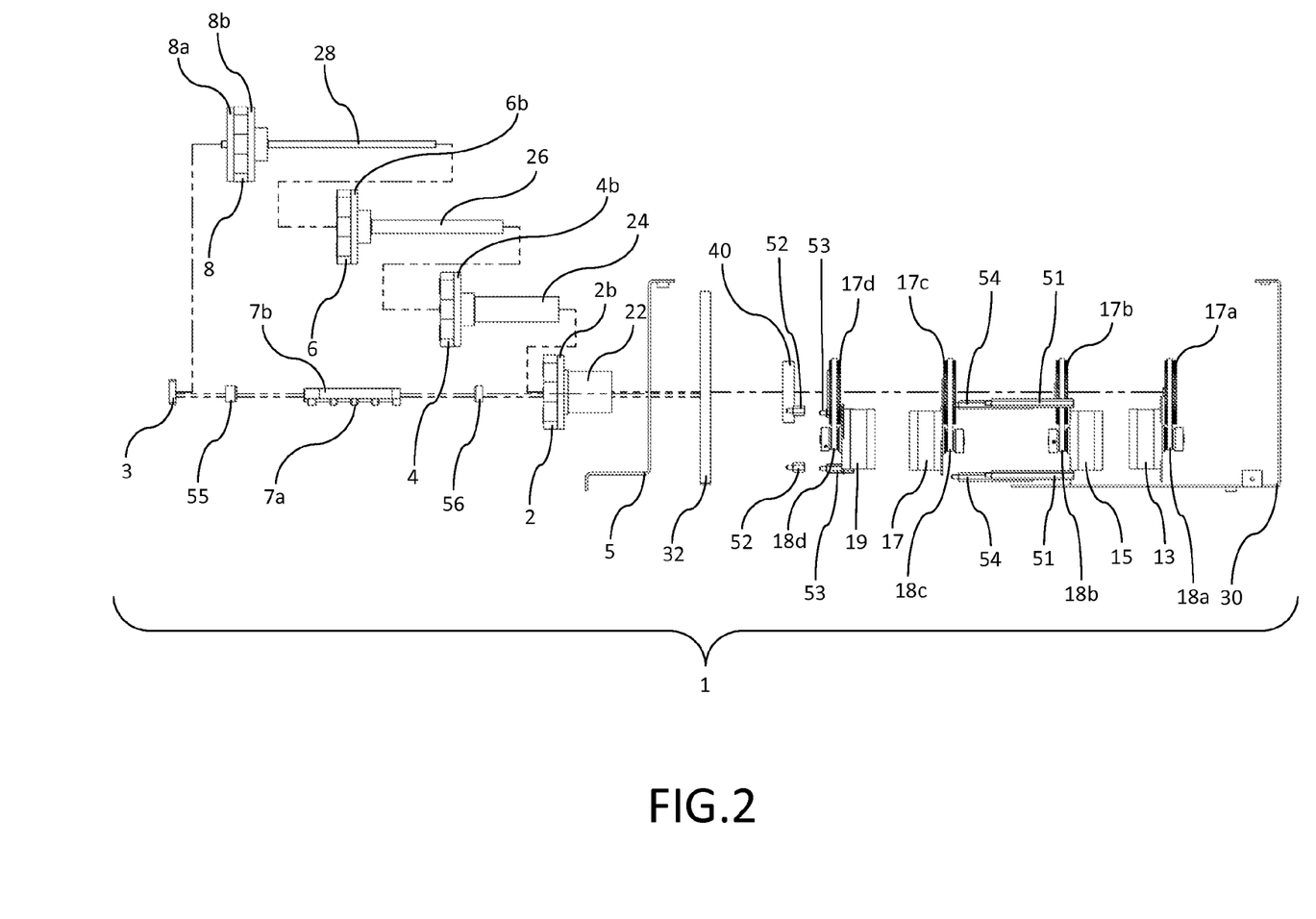
FIG. 2 provides an exploded side view of one embodiment of a multi-channel peristaltic pump.

Referring now to FIG. 2, the pump 1 is shown in an alternative view. It will be understood that the same numbers will be used for the same components shown in the various figures of the pump 1 and its components herein. In FIG. 2, an exploded view of the pump 1 is provided. As shown in FIG. 2, the pump 1 has four motors 13, 15, 17, and 19, and coupled to each is a belt, such as by attaching each to a belt 18a, 18b, and 18c, and 18d, respectively. When activated, each of motors 13, 15, 17, and 19 will drive movement of the belts 18a, 18b, 18c, and 18d, respectively. As described in more detail below, the movement of the belts 18a, 18b, 18c, and 18d will result in the movement of roller heads 2, 4, 6, and 8. The motors 13, 15, 17, and 19 may be conventional motors, such as those commercially available from Lin Engineering of Morgan Hill, Calif.

Referring now to FIG. 1, each of the roller heads 2, 4, 6, and 8 has a plurality of rollers attached thereto. The rollers of each of the roller heads 2, 4, 6, and 8 can vary in number, size and materials from the rollers of the other roller heads 2, 4, 6, and 8. As shown in FIG. 1, each of the roller heads 2, 4, 6, and 8 has a plate 2b, 4b, 6b, and 8b, respectively. As also shown in FIG. 1, each of the plates 2b, 4b, 6b, and 8b has one or more rollers attached thereto. In the embodiment shown in FIG. 1, the roller head 8 also has a second plate 8a, which is located between the rollers on roller head 8 and the support 3. As shown in FIG. 1, each of the plates 2b, 4b, 6b, and 8a and 8b are generally circular in shape in this embodiment.

In this embodiment of pump 1, the rollers of the roller heads 2, 4, 6, and 8 are made of polyethylene terephthalate (PET-P), and the roller flanges or rotors of the heads 2, 4, 6, and 8 are made of aluminum. The shafts or rotors 22, 24, 26, and 28 can be made of metals such as steel or stainless steel. It will be appreciated that the rollers, roller heads 2, 4, 6, and 8, and the rotors or shafts 22, 24, 26, and 28 can be made of a variety of materials as may be desired, including without limitation the following: for rollers: any type of low coefficient of friction material, for the flanges or rotors of the roller heads and shafts: structurally stable materials for supporting the rollers and to have enough strength for torsion and bending stresses on the hollow shafts, such as: aluminum and steel alloys. It will be appreciated that, although not shown in FIG. 1, the rollers attached to the roller heads press against tubing (also not shown in FIG. 1) which contains a fluid to be pumped, with the tubing held in place either against a casing (also not shown in FIG. 1) on the other side of the tubing from the rollers, or with the tubing held against the rollers by a cartridge (also not shown in FIG. 1) which can be removably attached to the pump 1, with the tubing located within the body of the cartridge.

In addition, each of the roller heads 2, 4, 6, and 8 has a corresponding shaft (shafts 22, 24, 26, and 28, respectively) extending in one direction from the plates 2b, 4b, 6b, and 8b of the roller heads 2, 4, 6, and 8. It will be seen that each of the shafts 22, 24, 26, and 28 are circular around an axis, and that the corresponding roller heads 2, 4, 6, and 8 are also circular around the same axis as their corresponding shafts 22, 24, 26, and 28. As shown in FIG. 1, the shafts 22, 24, 26, and 28 have different diameters, for reasons explained below. In FIG. 1, it can be seen that in this particular embodiment, shaft 28 has the smallest diameter, shaft 26 has the next smallest diameter, shaft 24 has a diameter greater than that of shaft 26, but less than that of shaft 22, and shaft 22 has the largest diameter. As further detailed below, each of the shafts 22, 24, and 26 has an internal hollow portion which is sized to receive and hold therein at least one of the other shafts 24, 26, and 28. In this embodiment, shaft 28 fits within the interior opening of shaft 26, which in turn fits within the interior opening of shaft 24, which in turn fits within the interior opening of shaft 22. Those skilled in the art will appreciate that the shafts 22, 24, 26, and 28 can have various diameters and that, depending on the outside diameters of the shafts 22, 24, 26, and 28, the interior openings of the other shafts may vary accordingly to receive and fit together. When assembled together, each of the shafts 22, 24, 26, and 28 are located concentric with respect to each other and each of the shafts 22, 24, 26, and 28, as well as the corresponding roller heads 2, 4, 6, and 8, are rotatable around the same axis.

Still referring to FIG. 1, it can be seen that the shafts 22, 24, 26, and 28 are to be connected to pulleys 17d, 17c, 17b and 17a, respectively. Each of the pulleys 17d, 17c, 17b, and 17a is rotatable around the same axis as the shafts 22, 24, 26, and 28 (and the roller heads 2, 4, 6, and 8). In addition, each of the pulleys 17d, 17c, 17b, and 17a has a belt 18d, 18c, 18b, and 18a, respectively, attached to it. The belts 18a, 18b, 18c, and 18d, in turn, are attached to motors 13, 15, 17, and 19, respectively. In operation, when any one or more of the motors 13, 15, 17, and 19 is actuated, the motors 13, 15, 17, and 19 can then move the belts 18a, 18b, 18c, and 18d, thereby rotating pulleys 17a, 17b, 17c, and 17d, respectively, and when pulleys 7a, 17b, 17c, and 17d are rotated, the shafts 28, 26, 24, and 22, respectively, are rotated. As noted, when shafts 22, 24, 26, and 28 are rotated, the corresponding roller heads 2, 4, 6, and 8 are rotated.

In the embodiment shown in FIG. 1, each of the shafts 22, 24, 26, and 28 have the roller heads 2, 4, 6, and 8, respectively, attached at one end and are coupled to a belt 18d, a8c, 18b, and 18a, respectively, at their other ends. The belts 18a, 18b, 18c, and 18d can be timing belts to provide for synchronous power transmission. Those skilled in the art will appreciate that, although the embodiment shown in FIG. 1 provides for a separate motor and belt for each of shafts 22, 24, 26, and 28, a single motor could be used to rotate two or more of the shafts 22, 24, 26, and 28. For example, a single motor could be coupled to both shafts 22 and 24, with separate motors and belts used to rotate each of shafts 26 and 28. In addition, those skilled in the art will appreciate that instead of the belts and pulleys described herein, gears or other mechanisms may be used to rotate the shafts.

In the embodiment shown in FIG. 1, each of the shafts 22, 24, 26, and 28 are able to rotate independently with respect to each other. This allows a user to actuate any one or more of motors 13, 15, 17, and 19 at the same time, at different times, at the same or different speeds, and in the same or different directions. Thus, in the embodiment shown in FIG. 1, each of the roller heads 2, 4, 6, and 8 may, depending on the selection of a user (which may include a computer preprogrammed to operate in accordance with computer software), rotate alone, rotate at a different speed from one or more of the other roller heads 2, 4, 6, and 8, and may rotate in a direction opposite from that of one or more of the other roller heads 2, 4, 6, and 8. It will be appreciated that this aspect allows an operator of the pump 1 a great deal of flexibility in use of the pump 1. Moreover, it will be appreciated that the rollers of the roller heads 2, 4, 6, and 8 can be varied in size, number, and material, so that the pump 1 provides an operator of the pump 1 with an even greater amount of flexibility and choice in terms of operations and applications.

It will also be appreciated that, although the embodiment shown in FIG. 1 includes eight (8) rollers on each of roller heads 2, 4, 6, and 8, a the number and size of the rollers on the roller heads 2, 4, 6, and 8 may be varied. For example, roller head 2 can have eight (8) rollers, roller head 4 can have six (6) rollers, roller head 6 can have six (6) rollers, and roller head 8 can have eight (8) rollers. Those skilled in the art will appreciate that varying the number and/or size of the rollers located on the roller heads 2, 4, 6, and 8 will provide the user with greater flexibility for a variety of applications.

Still referring to FIG. 1, it can be seen that the face plate 5 includes an opening 5b. In the embodiment shown in FIG. 1, the opening 5b is substantially circular in shape and has a diameter that will allow at least a portion of shaft 22 to extend therethrough. Also shown in FIG. 1 is a bearing 40. In the embodiment shown in FIG. 1, the bearing 40 is of a size and shape selected to fit in the opening 5b of the face plate 5. The bearing 40 can be of the same type of bearing as discussed below in connection with FIGS. 3 and 4. It will be understood that the bearing 40 has an interior opening through which shaft 22 (and the other shafts 24, 26, and 28 disposed within shaft 22) extends. The bearing 40 facilitates the rotation of shaft 22 within the opening 5b.

In addition, face plate 5 is adapted to be attached to a support 30. In the embodiment shown in FIG. 1, the support plate 30 provides both a bottom support and also a rear face for the pump 1. Those skilled in the art will appreciate that the motors 13, 15, 17, and 19 can all be attached to the bottom of the support 30, such as by any conventional attachment mechanisms, including screws, glue, adhesives and the like.

Referring now to FIG. 2, an exploded side view of the same embodiment of pump 1 is shown. As shown in FIGS. 1 and 2, the shafts 22, 24, 26, and 28 are of different diameters, and the size of each of the shafts 22, 24, 26, and 28 is selected to allow them to fit together in a concentric fashion. Shaft 28 can fit through and opening in roller head 6 and extend through the interior opening of shaft 26. Shaft 26, in turn, can fit through an opening in roller head 4 and extend through the interior opening of shaft 24. Shaft 24, in turn, fits through an opening in roller head 2 and extends through the interior opening of shaft 22. As noted above, this allows for the shafts 22, 24, 26, and 28 to be located concentric with respect to one another. In addition, this allows for the corresponding roller heads 2, 4, 6, and 8 to be located adjacent to at least one of the other roller heads 2, 4, 6, and 8, thus allowing the pump 1 to be of a more compact size than would otherwise be the case.

Figure 3:
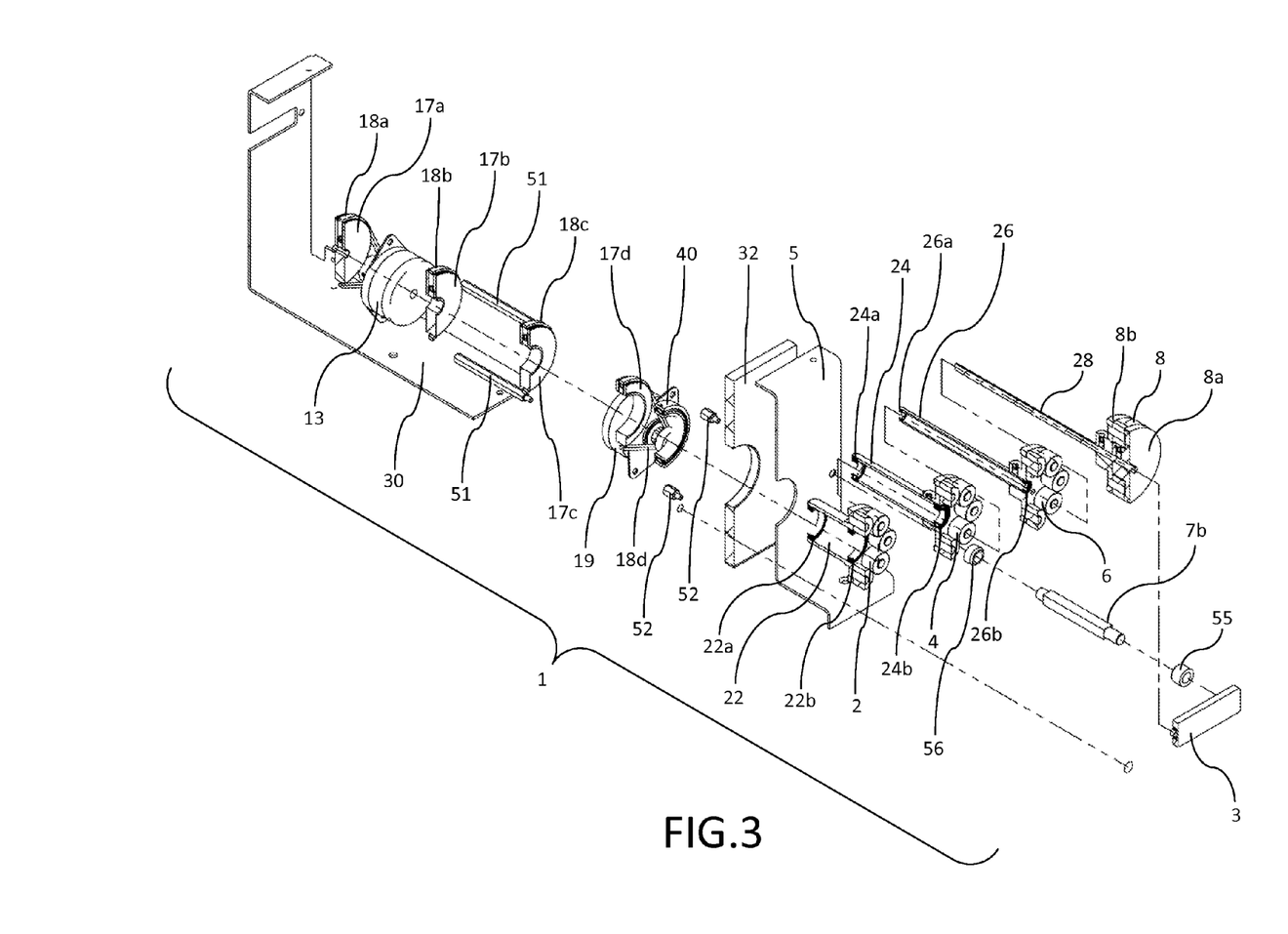
FIG. 3 provides an exploded cross-sectional view of one embodiment of a multi-channel peristaltic pump.

Now referring to FIG. 3, still another view of the pump 1 is provided. In FIG. 3, an exploded cross-sectional view of the pump 1 is provided. As before, the same numerals are used to indicate the same features and elements of pump 1 in FIG. 3. In the exploded, cross-sectional view of FIG. 3, the interior openings of the shafts 22, 24, and 26 can be seen more clearly. (In this particular embodiment, shaft 28 is solid and does not have an interior opening as do shafts 22, 24, and 26.) In addition, the openings in the roller heads 2, 4, and 6 can be seen more clearly. (In this particular embodiment, roller head 8 does not have an opening.)

Still referring to FIG. 3, it can be seen that the interior openings of each of shafts 22, 24, and 26 are circular in shape. As also shown in FIG. 3, located within shaft 22 are bearings 22a and 22b, located within shaft 24 are bearings 24a and 24b, and located within shaft 26 are bearings 26a and 26b. Each of the bearings 22a, 22b, 24a, 24b, 26a, and 26b are shown located at the respective ends of the interior openings of the shafts 22, 24, and 26, respectively. The bearings 22a and 22b facilitate and allow the easy rotation of shaft 24 when located within the interior opening of shaft 22. Similarly, the bearings 24a and 24b facilitate and allow the easy rotation of shaft 26 when located within the interior opening of shaft 24. In addition, the bearings 26a and 26b facilitate and allow the easy rotation of shaft 28 when located within the interior opening of shaft 26. Thus, the bearings 22a, 22b, 24a, 24b, 26a, and 26b help support the shafts 24, 26, and 28, respectively, while still allowing and facilitating the rotation of shafts 22, 24, 26, and 28 independently of the other of shafts 22, 24, 26, and 28.

It will be appreciated that in this embodiment, bearings 22*a* and 22*b* will be of a size selected to fit within the interior opening of shaft 22 and have an open internal diameter adapted to fit shaft 24. Similarly, bearings 24*a* and 24*b* will be of a size selected to fit within the interior opening of shaft 24 and have an open internal diameter adapted to fit shaft 26. Likewise, bearings 26*a* and 26*b* will be of a size selected to fit within the interior opening of shaft 26 and have an open internal diameter adapted to fit shaft 28. The bearings 22*a*, 22*b*, 24*a*, 24*b*, 26*a*, and 26*b* can be made of various materials, including without limitation the following: stainless steel and any other steel alloy combination. In addition, plastic or ceramics materials may be utilized too. The bearings 22*a*, 22*b*, 24*a*, 24*b*, 26*a*, and 26*b* can be conventional, such as those obtained from Misumi USA Inc. of Schaumburg, Ill. Bearings 22*a*, 22*b*, 24*a*, 24*b*, 26*a*, and 26*b* may be ball bearings or needle bearings of a size selected to fit snugly within the hollow interior portions of the shafts 22, 24, and 26, respectively. Alternatively, sleeve bearings or bushings could be used for bearings 22*a*, 22*b*, 24*a*, 24*b*, 26*a*, and 26*b*.

Figure 4:
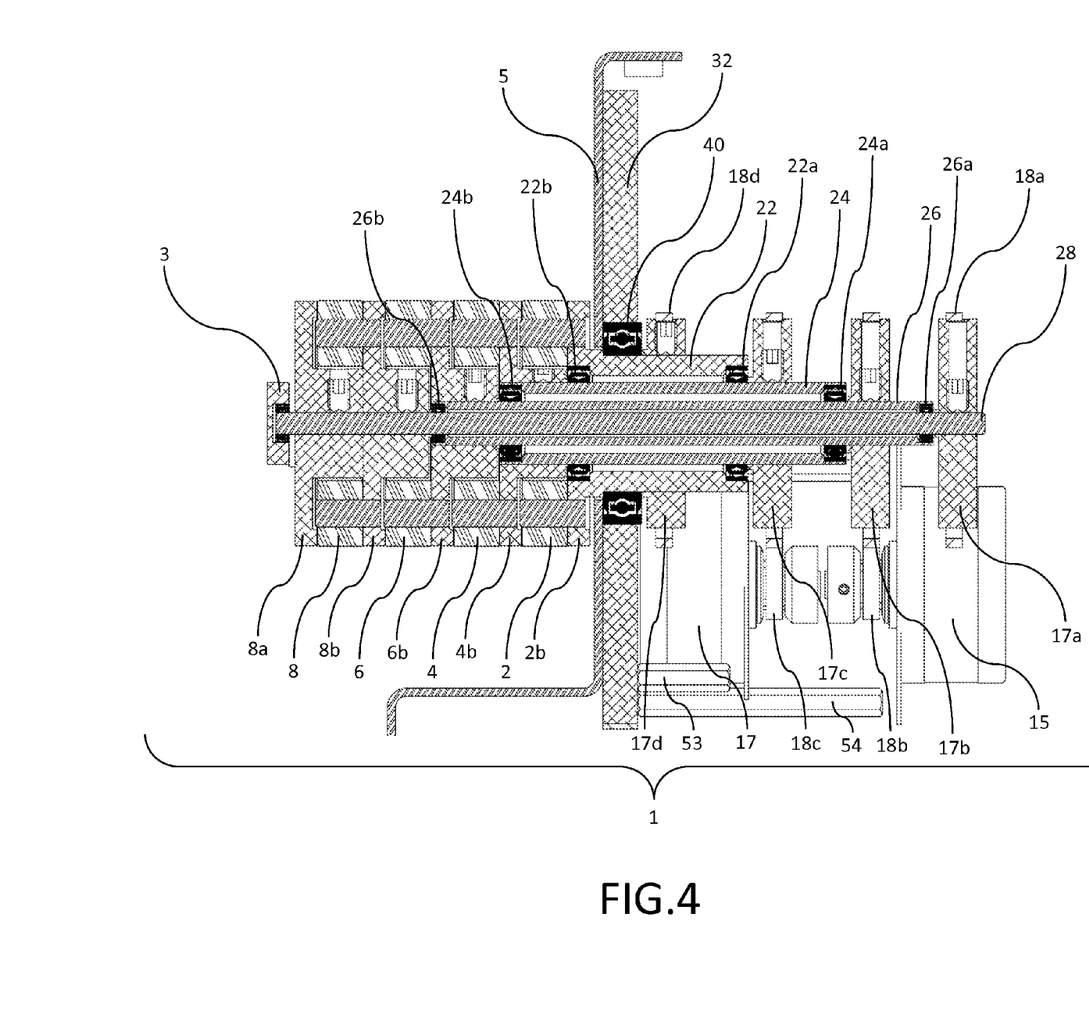
FIG. 4 provides a close-up sectional view of an embodiment of a multi-channel peristaltic pump.

Referring now to FIG. 4, a sectional view of the pump 1 as assembled is provided. It will be understood that for ease of reference, not all of the components of pump 1 as shown in FIGS. 1-3 and described above are numbered and labeled in FIG. 4. In FIG. 4, the shafts 22, 24, 26, and 28 are shown in a nested, concentric configuration, with shaft 28 located as the innermost, shaft 26 disposed about the outside of a portion of the length of shaft 28, shaft 24 disposed about the outside of a portion of the length of shaft 26 and shaft 28, and shaft 22 disposed outside of a portion of the length of shafts 24, 26, and 28. Although not shown in FIG. 4, it will be understood that each of the shafts 22, 24, 26, and 28 may be coupled to a motor, pulley and belt so that each of the shafts 22, 24, 26, and 28 may be rotated. In addition, roller heads 2, 4, 6, and 8 are shown in FIG. 4, as is the plate 8*a* of roller head 8.

In FIG. 4, bearing 40 is shown located within the opening 5*b* of the face plate 5 of the pump 1. Bearing 40 is also located within an opening in the support plate 32. Bearing 40 thus allows and facilitates the rotation of shaft 22 without friction or interference from face plate 5 or support plate 32. In addition, bearings 22*a*, 22*b*, 24*a*, 24*b*, 26*a*, and 26*b* are shown in FIG. 4. As shown in FIG. 4, bearings 22*a* and 22*b* are located within an inner diameter portion of the shaft 22, with bearing 22*a* located at or near a first end of the shaft 22 and bearing 22*b* located at or near the second end of shaft 22. Similarly, bearings 24*a* and 24*b* are disposed within the interior hollow portion of shaft 24, with bearing 24*a* located at or near a first end of the shaft 24 and bearing 24*b* located at or near a second end of the shaft 24. In addition, bearings 26*a* and 26*b* are shown located within the interior hollow opening of shaft 26, with bearing 26*a* located at or near a first end of the shaft 26 and bearing 26*b* located at or near a second end of the shaft 26. As noted above, the bearings 22*a*, 22*b*, 24*a*, 24*b*, 26*a*, and 26*b*, as well as bearing 40, allow the smooth rotation of the shafts 22, 24, 26, and 28 when the shafts are actuated and rotate. It will be appreciated that more or less bearings can be used than the number of bearings shown and described herein. In addition, the bearings 22*a*, 22*b*, 24*a*, 24*b*, 26*a*, 26*b*, and 40 can be of various types, such as those noted above, and need not be the same. Moreover, it should be noted that the locations of the bearings 22*a*, 22*b*, 24*a*, 24*b*, 26*a*, and 26*b* can be varied as may be desired.

Figure 5:
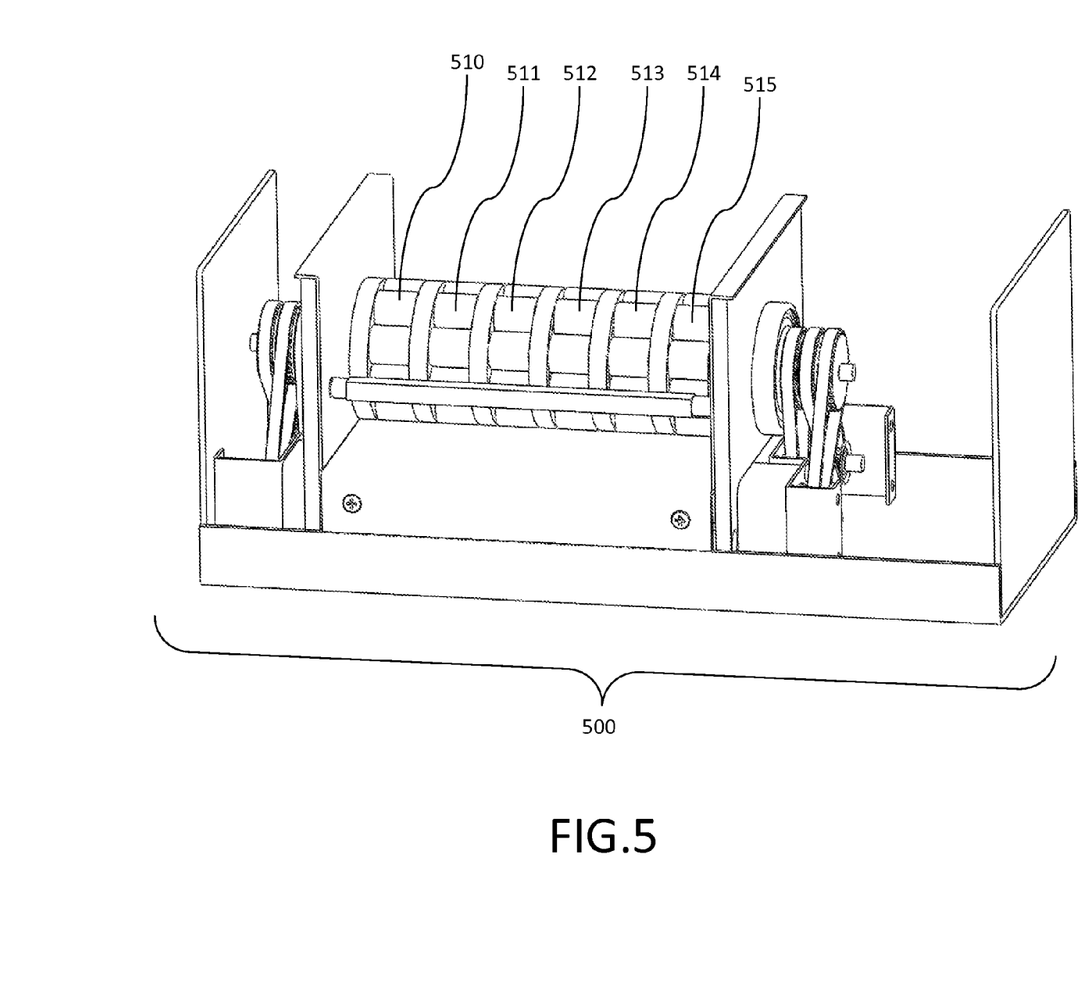
FIG. 5 provides a view of yet another embodiment of a multi-channel peristaltic pump.

In operation, a pump 1 in accordance with one or more embodiments herein can be provided with any desired number of roller heads, which may be 2 or more. In embodiments in which six, eight or more roller heads is desired, it may be desirable to locate the motors within the pump in such a way as to minimize the overall space needed for the pump 1. An embodiment intended to achieve this objective is shown in FIG. 5. In FIG. 5, and pump 500 is shown. Pump 500 includes six roller heads 510, 511, 512, 513, 514, and 515. Although not shown in FIG. 5, each of the roller heads 510, 511, and 512 has a shaft located concentric with the shafts of the other of the roller heads 510, 511, and 512. In addition, and although not shown, each of the roller heads 513, 514, and 515 has a shaft located concentric with the shafts of the other of the roller heads 513, 514, and 515. In addition, each of the shafts of the roller heads 510, 511, 512, 513, 514, and 515 is connected to a corresponding pulley (not shown for roller heads 510, 511, and 512) which, in turn, is connected to a motor (also not shown in FIG. 5 for roller heads 510, 511, and 512). Because the shaft for roller head 512 can fit within the shaft for roller head 511, which in turn can fit within the shaft for roller head 510, each of the roller heads 510, 511, and 512 can be connected to a separate motor (not shown) so that each of the roller heads 510, 511, and 512 can be rotated at a speed and in a direction independently of each of the other of roller heads 510, 511, and 512. In addition, the shaft for roller head 513 can fit within the shaft for roller head 514, which in turn can fit within the shaft for roller head 515, so that each of the roller heads 513, 514, and 515 can be connected to a separate motor (not shown), thus allowing each of the roller heads 513, 514, and 515 to be rotated at a speed and in a direction independently of each of the other of roller heads 513, 514, and 515. Thus, the pump 500 can provide six roller heads 510-515 that can be rotated independently of one another, thus allowing an operator to choose to operate any one or more at a speed and in a direction that is the same as or different from that of any one or more of the other roller heads 510-515. Moreover, as shown in FIG. 5, the three motors coupled to roller heads 510, 511, and 512 can be located at one end or one side of the pump 500, with the three motors coupled to roller heads 513, 514, and 515, respectively, located at the other end or side of the pump 500. By placing the motors towards the respective ends of the pump 500, the six roller heads 510-515 can be located much closer together, which allows for easier use and operation, as well as providing a more compact design for the pump 500.

The pump 1 can be provided with a processor and memory having programs or software stored therein for use in controlling the operation of the roller heads. It will be appreciated that the pump 1 can also have a display and one or more user input devices (such as a touch pad) by which the user can select various modes of operation for each of the roller heads. For example, the user may choose to use the input device so that the pump 1 will rotate a first roller head in a first direction and at a first speed, rotate a second roller head in the same direction but at a different speed, and also rotate a third roller head in a second direction and at a third speed. In this way, the pump 1 provides greater flexibility and ease of use for a greater variety of applications, yet maintains a compact size because multiple roller heads can be located closer together than in conventional peristaltic pumps that do not allow for such different modes of operation. For example, the pump 1 can be provided with a first roller head having six rollers of a first size, a second roller head with eight rollers of a second size, and also a third roller head with ten rollers of still a third size. Those skilled in the art will appreciate that the selection of the number and sizes of the rollers on the roller head can be made to provide greater control over the volumes and flow rate of the fluid to be pumped by the pump 1. Control over such variables, together with control over the speed and direction of movement of each of the roller heads, provides the operator with a substantial amount of flexibility and control.

Figure 6:
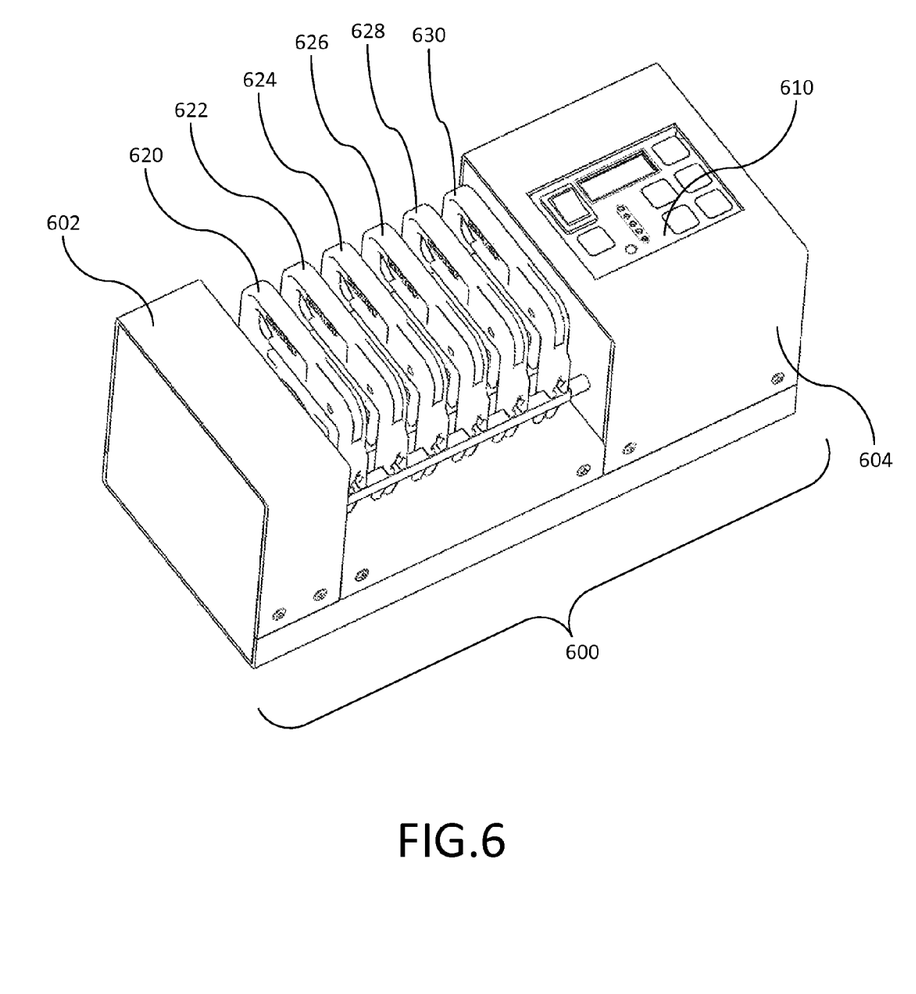
FIG. 6 provides a view of still another embodiment of a multi-channel peristaltic pump.

Referring now to FIG. 6, an alternative embodiment of a peristaltic pump 600 is provided. In FIG. 6, a pump 600 is shown. The pump 600, like the pump 500 shown in FIG. 5, includes six roller heads (not shown) coupled to six separate motors (not shown), with three of the motors located at or near a first end 602 of the pump 600, and the other three motors located at or near the second end 604 of the pump 600. As shown in FIG. 6, six removable cartridges 620, 622, 624, 626, 628 and 630 are attached to the pump 600. These cartridges may be of a conventional type, such as those disclosed in U.S. Pat. No. 7,214,038, and such as those commercially available from Ismatec, S.A., of Glattbrugg, Switzerland. As also shown in FIG. 6, casing is provided for pump 600 to cover the motors and other components, including the processor, memory, and other components needed for controlling the operation of the pump 600. In addition, pump 600 includes a display 610, which provides for the display of information and also allows a user to input data and control or program the operation of the pump 600, such as by programming the speed and direction of the six roller heads to which cartridges 620, 622, 624, 626, 628, and 630 are removably attached.

It will be appreciated that the foregoing description and the Figures are illustrative embodiments only and do not define the scope of the invention, which is defined by the scope of the claims. Those skilled in the art will appreciate that a variety of modifications and changes may be made to the embodiments described in detail herein without departing from the scope and spirit of the invention, which is defined only by the claims. For example, a different number of roller heads, motors, and the like may be used, and a variety of different materials may be used as well. In addition, the motors may be coupled to the shafts of the roller heads in different ways, and the motors may be of different types than those described herein. Similarly, removable cartridges need not be used, but may be desirable for ease of use and convenience.

I claim:

1. A peristaltic pump comprising:
at least three motors;
at least three rotor shafts, each of which rotates around a shared axis and each of which can rotate independently of the other of said rotor shafts, with a portion of a first one of said rotor shafts located within a portion of a second one of said rotor shafts, and with at least portions of the first and second of said rotor shafts located within a portion of a third one of said rotor shafts;
a first, second, and third plurality of rollers attached to a first end of each of said first one, second one, and third one of said rotor shafts, respectively, wherein each of said first, second, and third plurality of rollers have substantially the same width, and wherein said first, second, and third plurality of rollers move around the axis as said rotor shaft to which said plurality of rollers are attached moves, and wherein each of said first, second, and third plurality of rollers compresses at least a portion of a first, second, and third tubing, respectively, when the portion of each of the first, second, and third tubing is located within a first, second, and third removable cartridge, respectively, when the first, second, and third removable cartridges having the portion of each of the first, second, and third tubing therein, respectively, are attached to the first end of the first one, second one, and third one of said rotor shafts to which said first, second, and third rollers is attached when said first, second, and third plurality of rollers rotates around the shared axis;
at least three belts, with each of said belts coupling at least one of said motors to at least one of said rotor shafts; and
a control system comprising a processor and memory having instructions stored therein for allowing an operator to selectively actuate each of said rotor shafts at a selected speed and in a selected direction, wherein the speed and direction of each of said rotor shafts may be independent from the speed and direction of each of the other of said rotor shafts, and wherein each of said rotor shafts can be actuated at a different time or at the same time as one or more of the other of said rotor shafts.

2. The pump according to claim 1 wherein said pump comprises at least four motors, at least four rotors and at least four belts.

3. The pump according to claim 1 wherein said pump comprises at least five motors, at least five rotors and at least five belts.

4. The pump according to claim 1 wherein the number of rollers attached to at least one of the rotors is different from the number of rollers attached to at least one of another of said rotor shafts.

5. The pump according to claim 4 wherein said pump comprises at least four rotors.

6. The pump according to claim 5 wherein said pump comprises at least five rotors.

7. A peristaltic pump comprising:
at least first, second, and third motors;
at least first, second, and third rotor shafts, with said first rotor shaft coupled to said first motor, said second rotor shaft coupled to said second motor, and said third rotor shaft coupled to said third motor, wherein each of said first, second, and third rotor shafts is adapted to rotate around a shared axis and each of said first, second and third rotor shafts is adapted to rotate independently of the other of said first, second, and third rotor shafts, with at least one of said first, second, and third rotor shafts having a hollow portion through which at least portions of two of the other of said first, second, and third rotor shafts extend and with at least two of said first, second, and third rotor shafts each having a hollow portion through which a portion of at least one of the other of said first, second, and third rotor shafts extends;
a first, second, and third plurality of rollers, each having substantially the same width, attached to a first end of each of said first, second, and third rotor shafts, respectively, wherein said first, second, and third plurality of rollers move around the axis as said rotor shaft to which said rollers are attached moves, and wherein, when each of said first, second and third rotor shaft move, each of said first, second, and third plurality of rollers compresses at least a portion of a first, second, and third tubing, respectively, when the portion of each of the first, second, and third tubing is located within a first, second and third removable cartridge, respectively, and when the first, second, and third removable cartridge is attached to the first end of the first, second, and third rotor shafts to which said first, second, and third plurality of rollers is attached; and a control system comprising a processor for executing computer software allowing an operator to selectively actuate each of said first, second, and third rotor shafts at a selected speed and in a selected direction.

8. The peristaltic pump according to claim 1 further comprising at least three cartridges which comprise tubing for holding a fluid, wherein one of said cartridges is removably attached to the first end of each of the first one, second one, and third one of said rotor shafts.

9. The peristaltic pump according to claim 7 wherein the pump comprises:

at least five motors;

at least five rotor shafts, wherein at least two of said rotor shafts each having a hollow portion through which at least a portion of a third rotor shaft extends, and wherein at least three of said motors are located proximal a first end or side of the pump, with two of said at least five motors located proximal a second end or side of the pump.

10. The peristaltic pump according to claim 7 further comprising a display, wherein said display further comprises an input device allowing a user to input information to be used by the computer software.

11. The peristaltic pump according to claim 10 wherein the computer software comprises instructions which, when executed by said processor, cause the motors, and thereby the rollers, to move in accordance with selected criteria.

12. The peristaltic pump according to claim 11 wherein said criteria comprise speed and direction.

13. A dosing system for administering medicine, comprising:

a plurality of tubes for fluid transmission, a peristaltic pump comprising:

at least first, second, and third motors;

at least first, second, and third rotor shafts, each of which rotates around a shared axis and each of which can rotate independently of the other of said first, second, and third rotor shafts, with a portion of said first rotor shaft located within a portion of said second and third of said rotor shafts, and with a portion of said second rotor shaft located within a portion of said third rotor shaft;

a first, second, and third plurality of rollers attached to a first end of each of said first, second, and third rotor shafts, respectively, so that said plurality of rollers move around the axis as said first, second, and third rotor shaft to which said rollers are attached moves, wherein, when each of said first, second and third rotor shaft moves, each of said first, second, and third plurality of rollers compresses a portion of a first, second, and third tube, respectively, wherein the portion of the first, second, and third tube is located within a first, second, and third removable cartridge, respectively, when the first, second, and third removable cartridge is attached to the first end of the first, second, and third rotor shafts, respectively, to which said first, second, and third plurality of rollers is attached;

at least first, second, and third belts, with each of said belts coupling at least one of said motors to at least one of said rotor shafts; and a control system operable for selectively actuating each of said motors to thereby cause each of said plurality of rollers to move at a selected speed and in a selected direction, wherein at least a portion of an outer diameter of each of said tubes is removably coupled to at least one of said rollers such that movement of the at least one of said rollers is adapted to pump a fluid in said tube.

14. The pump according to claim 1 wherein said pump further comprises a first end and a second end, and wherein said plurality of rollers is proximate said first end.

15. The pump according to claim 1 wherein said pump further comprises a first end and a second end and a face proximate said first end, wherein said plurality of rollers is proximate said face.

16. The pump according to claim 1 wherein said pump further comprises a first end and a second end and a housing, wherein said housing comprises a face proximate said first end and wherein said plurality of rollers extends from said face.

17. The pump according to claim 7 wherein said pump further comprises a first end and a second end, and wherein said plurality of rollers is proximate said first end.

18. The pump according to claim 7 wherein said pump further comprises a first end and a second end and a face proximate said first end, wherein said plurality of rollers is proximate said face.

19. The pump according to claim 7 wherein said pump further comprises a first end and a second end and a housing, wherein said housing comprises a face proximate said first end and wherein said plurality of rollers extends from said face.

20. The dosing system according to claim 13 wherein said pump further comprises a first end and a second end, and wherein said plurality of rollers is proximate said first end.

21. The dosing system according to claim 13 wherein said pump further comprises a first end and a second end and a face proximate said first end, wherein said plurality of rollers is proximate said face.

22. The dosing system according to claim 13 wherein said pump further comprises a first end and a second end and a housing, wherein said housing comprises a face proximate said first end and wherein said plurality of rollers extends from said face.

23. The pump according to claim 7 further comprising at least a fourth motor and at least a fourth rotor shaft.

24. The pump according to claim 7 further comprising at least a fifth motor and at least a fifth rotor shaft.

25. The peristaltic pump according to claim 7 wherein a first end of the first rotor shaft is located proximal a first end of the second rotor shaft, and wherein the first end of the second rotor shaft is also located proximal a first end of the third rotor shaft, and wherein a second end of the first rotor shaft is located proximal the first motor, a second end of the second rotor shaft is located proximal the second motor, and a second end of the third rotor shaft is located proximal the third motor.

* * * * *